United States Patent [19]

Sartore

[11] Patent Number: 5,703,361
[45] Date of Patent: Dec. 30, 1997

[54] CIRCUIT SCANNING DEVICE AND METHOD

[75] Inventor: Richard G. Sartore, Bradley Beach, N.J.

[73] Assignee: The United States of America as represented by the Secretary of the Army, Washington, D.C.

[21] Appl. No.: 649,826

[22] Filed: Apr. 30, 1996

[51] Int. Cl.[6] .................. G01N 23/225; H01J 37/256; H01J 37/28
[52] U.S. Cl. .................................... 250/310; 250/307
[58] Field of Search .................................... 250/310, 307

[56] References Cited

U.S. PATENT DOCUMENTS

| H993 | 11/1991 | Sartore | 250/307 |
|---|---|---|---|
| 3,829,691 | 8/1974 | Hufnagel | 250/307 |
| 4,777,364 | 10/1988 | Sartore | 250/307 |
| 5,414,265 | 5/1995 | Sartore | 250/310 |

OTHER PUBLICATIONS

Sartore, Richard G., "Defect Detection and Thickness Mapping of Passivation Layers on Integrated Circuits Using Energy Dispersive X-Ray Analysis and Image Processing Techniques", Scanning Microscopy, vol. 2, No. 3, 1988, pp. 1383–1395.

Primary Examiner—Jack I. Berman
Attorney, Agent, or Firm—Michael Zelenka; John M. O'Meara; William H. Anderson

[57] ABSTRACT

A circuit scanning device for use in mapping the lateral dimensions and positions of a conductive layer of an integrated circuit is provided. The device includes a scan control, a scanning electron microscope, an x-ray detector, a map maker, an algorithm storage unit, and an algorithm selector whereby an IC chip is irradiated with an electron beam, which is raster scanned across the IC chip. The x-ray radiation emission is then monitored and the electron beam is adjusted so as to produce an enhanced map of the conductive layers on the IC chip.

1 Claim, 1 Drawing Sheet

CIRCUIT SCANNING DEVICE AND METHOD

GOVERNMENT INTEREST

The invention described herein may be manufactured, sold, imported, used and licensed by or for the Government of the United States of America without the payment to me of any royalties thereon.

FIELD OF THE INVENTION

The invention described herein generally relates to a circuit scanning device and method, and in particular the invention relates to a circuit scanning device and method, for making an enhanced map of a metal circuit covered by an insulation layer, by setting and adjusting magnification and voltage and scan of a scanning electron microscope, using a plurality of selective algorithms.

BACKGROUND OF THE INVENTION

The prior art circuit scanning device and method is described in U.S. Pat. No. 4,777,364, issued Oct. 11, 1988, to the abovenoted inventor. A related patent is U.S. Pat. No. 5,414,265, issued May 9, 1995, to the abovenoted inventor. Both of these patents are incorporated by reference hereto. A related publication is Scanning Microscopy, Vol. 2, No. 3, 1988, pages 1383–1395.

The prior art circuit scanning device includes, a computer which has a scan control unit and a memory store, a scanning electron microscope which is controlled by the scan control and which delivers an electron beam to a chip workpiece that emits x-ray intensities, an x-ray detector which provides signals to the memory store, and a cathode ray tube which is connected to the memory store and which shows an x-ray picture.

One problem with the prior art circuit scanning device is that the inspection of the chip workpiece or circuit board is sometimes unreliable.

A second problem is that the x-ray map of metal film and insulation layer of the chip workpiece is not always clear enough for analysis thereof.

A third problem is that the x-ray map as acquired has a need to be enhanced, in order to better inspect the chip workpiece, for use in finding lateral position and dimensions of conductive or insulative layers, and for use in reverse engineering of the chip workpiece.

SUMMARY OF THE INVENTION

According to the present invention, a circuit scanning device is provided. This device comprises a computer which has a scan control unit and a memory store, a scanning electron microscope which delivers an electron beam to a chip workpiece subsurface point that emits x-ray intensities, an x-ray detector which provides signals to the memory store, a map maker which is connected to the memory store and which provides an enhanced x-ray map, and an algorithm storage unit which delivers a selective series of magnification signals and a selective series of voltage signals to the scanning electron microscope and which delivers a selective series of signals to the scan control unit for transmission by the scan control unit of a selective series of scan signals to the scanning electron microscope.

By using the algorithm storage unit, a selective algorithm can be used for making a selective, enhanced x-ray map. This enhanced map can be studied alone or in conjunction with a prior art or standard map, so that the problem of making an unreliable inspection of a chip workpiece is minimized.

Also, according to the present invention, a method is provided of mapping the lateral dimensions and positions of conductive and insulated layers of an integrated circuit, the integrated circuit having conductive material disposed on a surface of a body of substrate material, the conductive and substrate material being coated with an insulation material, the conductive and substrate and insulation materials each having different respective x-ray radiation outputs in response to input electron irradiation, the method comprising the steps of:

irradiating an area of interest of the surface of the substrate body and the conductive material with a beam of electrons of a sufficient level of energy to penetrate the insulation material and to interact with at least the conductive material to cause the conductive material to produce its x-ray radiation output;

raster x-y scanning the beam of electrons over the area of interest of the substrate body and the conductive material and monitor the x-ray radiation output therefrom in synchronism with the scanning of the beam in order to form a map of the x-ray radiation output that is generated during said scanning of the beam of electrons;

adjusting the level of energy of the beam of electrons for setting a predetermined extent of penetration of the beam;

adjusting the raster x-y scanning of the beam of electrons for setting a predetermined number of coordinate x-y points on the map of the x-ray radiation output; and enhancing x-ray maps according to the present invention, as an example, to reduce noise and provide reliable detection of conductive layers in an automated fashion.

BRIEF DESCRIPTION OF THE DRAWINGS

The foregoing and other objects, features and advantages will be apparent from the following description of the preferred embodiment of the invention as illustrated in the accompanying drawing.

DESCRIPTION OF THE PREFERRED EMBODIMENT

Figure 1:
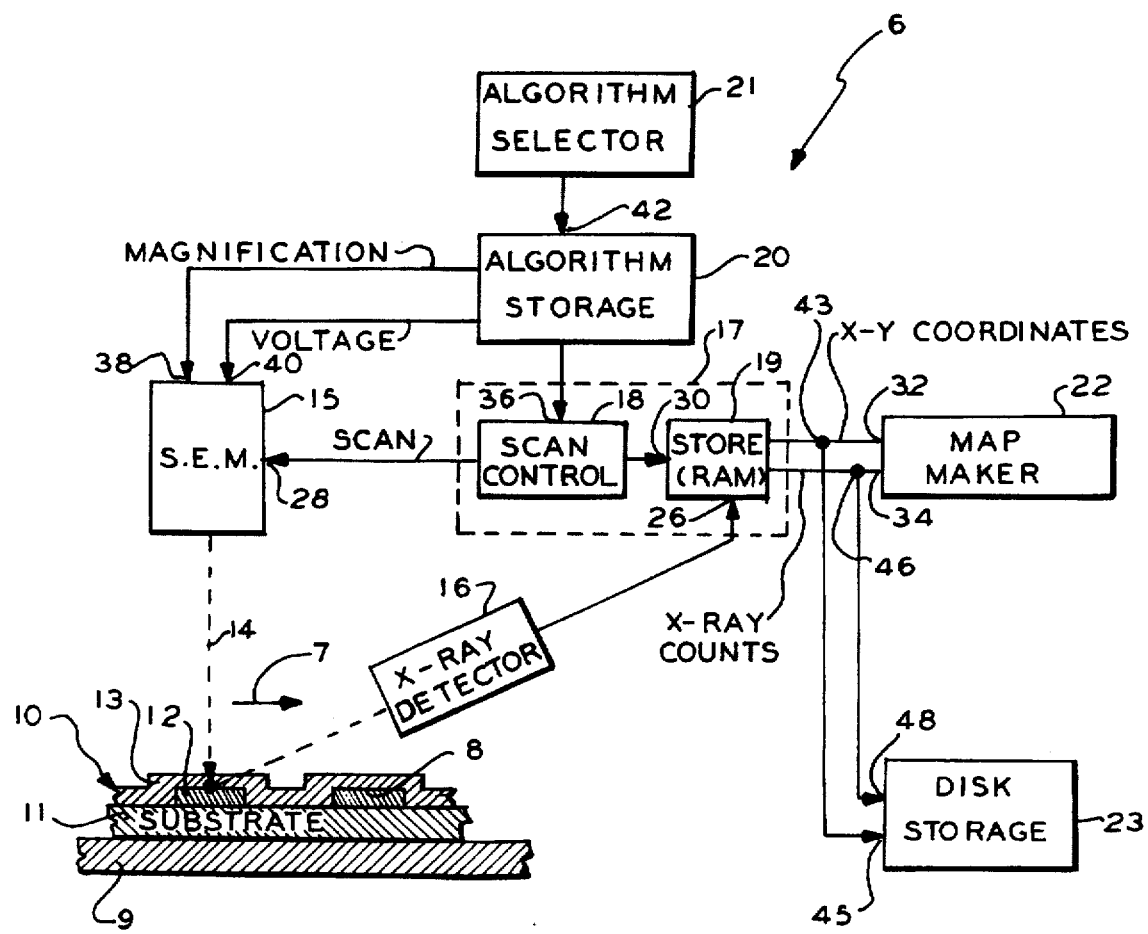
FIG. 1 is a schematic block diagram, partly in section, of a circuit scanning device according to the present invention.

As shown in FIG. 1, a circuit scanning machine or device 6 is provided. Device 6 scans in a scanning direction 7, in parallel courses, over an integrated circuit (IC) 10. Integrated circuit or chip 10 rests on a support plate 9. Integrated circuit 10 has a substrate 11. Substrate 11 has aluminum film or strips or conductive line traces or first and second traces 12, 8. Traces 12, 8 are covered with a passivation or insulation layer 13. Substrate 11 is a silicon material. Insulation layer 13 is a silicon dioxide material.

Device 6 is intended to detect holes and thickness non-uniformity in the insulation layer 13. Device 6 has a scanning electron microscope (SEM) 15, which generates an electron beam 14. Beam 14 impinges upon the integrated circuit (IC) 10. Beam 14 interacts with the materials in the chip 10 to generate x-rays. The x-rays are detected by an x-ray detector 16. The x-rays from the insulation layer 13 and from the aluminum film 12 are distinct, since they are of different wavelengths. The measured x-ray intensity provides a direct indication of the thickness of insulation layer 13.

Device 6 also has a computer 17. Computer 17 has a scan control apparatus 18 and has a storage capacity or store 19.

Store 19 is a random access memory (RAM). Scan control 18 develops the x and y coordinates, or raster scan signals, which are delivered to the SEM 15. The raster scan signals generated by the scan control 18 are also coupled to the store 19, as are the x-ray counts from the scanned points or pixels. Computer 17 may be Digital Equipment Corp., computer, or the like.

Device 6 also has an algorithm storage 20, which has an algorithm readout unit (not shown) for delivering magnification signals and voltage signals and scan signals to SEM 15. Algorithm storage 20 has an algorithm selector 21 for selecting an algorithm disposed therein.

The stored x-ray counts correspond spatially to the x-rays generated by the impingement of the electron beam 14 as it is scanned over the points or pixels of the aluminum film of the chip 10. After storage, the stored raster of x-ray counts is read out and delivered to a map making unit or printer or map maker 22. By using a map of signals of the x-rays from the aluminum sublayer 12 of the chip 10, the lateral dimensions and location in an x-y plane of the conductive layers can be detected. The insulation layer 13 x-ray signal is used to enhance the conductive layer signal (due to the complementary nature of the image) and provide a more reliable extraction of lateral location. Also, the x-ray signals are delivered to a cathode ray tube (not shown), and to a disk storage or store 23 for image storing.

Scan control apparatus 18 connects to the algorithm, or program or software, storage unit 20, which has the algorithm or program or software selector unit 21. The map maker 22 delivers an x-ray map (not shown).

The scanning electron microscope (SEM) 15, x-ray detector 16, computer 17, algorithm storage 20, algorithm selector 21, map maker 22, and the disk storage unit 23 are standard commercial units. In a prior device by the same inventor, SEM 15 was an AMR 1700 SEM; and computer 17 was part of a Tracor Northern 5500 x-ray analyzer with Microscan for computer controlled x-y scan by E-beam 14.

Detector 16 is connected to an input 26 of RAM store 19. Scan control 18 is connected to an input 28 of SEM 15 and to an input 30 of RAM store 19. RAM store 19 is connected to an input 32 of map maker 22 and to an output 34 of map maker 22. Algorithm storage 20 is connected to an input 36 of scan control 18 and to an input 38 of SEM 15. Algorithm storage 20 also is connected to an input 40 of SEM 15. Selector 21 is connected to an input 42 of algorithm storage 20. RAM store 19 is also connected to an input 45 of disk storage 23 via junction 43. Output 34 of map maker 22 is also connected to an input 48 of disk storage 23 via junction 46.

An enhanced map is made by using a selective enhanced algorithm. The enhanced algorithm directs a series of signals to scan control 18 and SEM unit 15. This enhanced algorithm provides magnification signals, in series, and provides voltage signals, and provides scan signals through scan control 18 to SEM unit 15.

SEM unit 15 projects electron beam 14 onto integrated circuit chip 10. Electron beam 14 induces an x-ray emission from IC chip 10. The x-ray emission is then detected by detector 16, which provides an input signal to RAM store 19. RAM store 19 also receives scan signals from conductor 29. RAM store 19 provides x-ray count signals to enhanced map maker 22. Store 19 also provides x-y coordinate signals to map maker 22.

In general, by increasing the voltage in incremental steps until the electrons have just enough energy to penetrate the thickness of the silicon dioxide or insulation layer 13, the thickness of layer 13 is determined. Then, the voltage is increased slightly, and SEM 15 scans the chip 10 in x-y directions in a raster manner, to obtain the map of lateral dimensions and locations of conductive layers on chip 10.

A number of different enhanced maps can be made from a number of enhanced algorithms. Each enhanced map will provide better definition of the conductive layers of chip 10. Each enhanced algorithm will be explained as follows.

A first algorithm is used for integrating the extraction of multiple, spaced x-ray map portions obtained at various locations on the chip with the operation of stitching together or joining x-ray map portions. The spacing and location of the x-ray map portions are set by the series of scan signals from scan control 18.

A second algorithm is used for stepping from one location to another location on the chip, and making an x-ray map at each location, and using a selective magnification value and a selective penetration voltage at each location. The stepping from one location to another is set by the series of scan signals from scan control 18. The magnification and voltage are set by the respective signals from storage 20.

A third algorithm is used for forming a seamless mosaic of x-ray maps for reconstructing the arrangement and spatial information of the metal layer. Layer information is extracted using penetration voltage. Spatial x-y dimensions are obtained using magnification. The voltage and magnification are set by the respective signals from the algorithm storage 20.

A fourth algorithm is used to provide multiple magnifications at different areas of the map, for detail studies. The areas are set by the series of scan signals from scan control 18. The respective magnifications are set by the series of signals from algorithm storage 20.

A fifth algorithm is used to make the standard file layouts of all acquired maps, for ease of filing. The scale of an acquired map is set by the magnification signals from algorithm storage 20.

A sixth algorithm is used to make a standard file layout and then to make a metal image map. Then, the standard file layout is compared to the metal image map.

A seventh algorithm is used to make a two-layer map of the aluminum film and silicon dioxide insulation layer, and then to make a one-layer map of silicon dioxide layer only. Then, subtract the map of aluminum or conductive layers only from the map of aluminum film and silicon dioxide insulation layer so as to enhance the aluminum film map.

An eighth algorithm is used to smooth out a basic x-ray map by averaging each spatial dimension with its four neighboring spatial dimensions, or a like procedure. The smoothing procedure reduces noise in non-metal regions of the map, and helps to define the edges of the metal layer.

According to the invention, there is provided a method of mapping the lateral location of a conductive layer 12 of an integrated circuit 10 which has an insulation material 13 disposed on a surface of a body of substrate material 11, the conductive and substrate material being coated with an insulation material 13, the conductive and substrate and insulation materials each having different respective x-ray radiation outputs in response to input electron irradiation. This method comprises the steps as indicated hereafter.

Irradiate the area of interest of the surface of the substrate body and the conductive material with a beam 14 of electrons of sufficient level of energy to penetrate the insulation material 13 and to interact with at least the conductive material to cause the conductive material to produce an x-ray radiation output.

Raster scan the beam 14 of electrons across the area of interest of the surface of the substrate body and the conductive material and monitor the x-ray radiation output therefrom in synchronism with the scanning of the beam in order to map the x-ray radiation output that is generated during said scanning of the beam of electrons.

Adjust the level of energy of the beam of electrons 14 by setting a predetermined extent of penetration of the beam 14.

Adjust the raster scan by setting a predetermined number of coordinate x-y points on the x-ray map.

The advantages of circuit scanning device 6 and the method of making an enhanced map, are indicated hereafter.

A) Device 6 minimizes any unreliability in the inspection of a metal film of an integrated circuit.

B) Device 6 minimizes unclearness in an x-ray map of a metal film and insulation layer of a chip workpiece.

C) Device 6 enhances a basic x-ray map in order to find lateral dimensions and positions of conductive or insulation layers in an IC chip.

While the invention has been described in its preferred embodiment, it is to be understood that the words which have been used are words of description rather than limitation and that changes maybe made within the purview of the appended claims without departing from the true scope and spirit of the invention in its broader aspects.

For example, a multi-circuit board can be inspected by mapping each separate circuit, during manufacture, before its successive circuit is added.

What is claimed is:

1. A method for mapping the overall layout and lateral dimensions of a conductive layer in an integrated circuit having a body of substrate material that includes a surface on which the conductive layer is disposed and having a coating of an insulation material disposed thereover; the conductive layer, body of substrate material and insulation material each having different x-ray radiation output in response to electron irradiation inputs, the method comprising the steps of;

scanning an area of interest on the integrated circuit with a beam of electrons having the energy level thereof adjusted to irradiate both the insulation material and the conductive layer;

monitoring x-ray radiation synchronously with the scanning, at X-Y pixel locations within the area of interest;

storing a first map of the x-ray radiation monitored at each X-Y pixel location during the scanning;

rescanning the area of interest with a beam of electrons having the energy level thereof adjusted to irradiate the insulation material only;

monitoring the x-ray radiation synchronously with the rescanning, at the X-Y pixel locations;

storing a second map of the x-ray radiation monitored at each X-Y pixel location during the rescanning;

subtracting the x-ray radiation monitored at each X-Y pixel location for the second map from the x-ray radiation monitored at each X-Y pixel location for the first map, to derive a third map from the x-ray radiation that relates to only the conductive layer at each X-Y pixel location.

* * * * *